United States Patent [19]
Hobbs et al.

[11] Patent Number: 5,430,192
[45] Date of Patent: Jul. 4, 1995

[54] POLYSULFIDE SEALANTS WITH REDUCED MOISTURE VAPOR TRANSMISSION

[75] Inventors: Steven J. Hobbs, Woodstock; Keith B. Potts, Elgin; John W. Nuber, McHenry; John R. Gilmore, Crystal Lake, all of Ill.

[73] Assignee: Morton International, Inc., Chicago, Ill.

[21] Appl. No.: 112,729

[22] Filed: Aug. 26, 1993

[51] Int. Cl.$^6$ .......................... C07C 321/04
[52] U.S. Cl. .......................... 568/22
[58] Field of Search .......................... 568/22

[56] References Cited

U.S. PATENT DOCUMENTS

| | | | |
|---|---|---|---|
| 2,363,614 | 11/1944 | Patrick | 260/79 |
| 2,363,615 | 11/1944 | Patrick | 260/42 |
| 2,363,616 | 11/1944 | Patrick | 260/42 |
| 2,466,963 | 4/1949 | Patrick et al. | 260/79.1 |
| 2,553,206 | 5/1951 | Patrick | 260/79.1 |
| 3,736,301 | 5/1973 | Berenbaum et al. | 260/79 |

FOREIGN PATENT DOCUMENTS 0547905 6/1993 European Pat. Off. .
302270 8/1929 United Kingdom .

Primary Examiner—Johann Richter
Assistant Examiner—John Peabody
Attorney, Agent, or Firm—Robert M. Didrick; Gerald K. White

[57] ABSTRACT

The moisture vapor transmission rates of sealants containing liquid polysulfides made from mixtures of a hexylene dihalide and a chloroethyl formal wherein the molar ratio is from about 1.5:1 to about 2.3:1 are extremely low. A preferred ratio is 0.64:0.36. The new liquid polysulfide is useful in conventional sealant formulations for insulated glass window units.

2 Claims, No Drawings

POLYSULFIDE SEALANTS WITH REDUCED MOISTURE VAPOR TRANSMISSION

BACKGROUND OF THE INVENTION

This invention relates to liquid polysulfides and sealants made therefrom whose moisture Vapor transmission rates are extremely low. More particularly, it relates to liquid polysulfides made from mixtures of an alkylene dihalide and a chloroethyl formal.

Oligomeric polysulfides based on bis-(2-chloroethyl formal) have been available commercially for over 30 years. These polymers are made in two steps, the first of which is a dispersion polymerization of the formal with sodium polysulfide in water. In the second step, the high molecular weight (about 100,000) polymer is reductively cleaved with sodium hydrosulfide and sodium sulfite to a material whose sulfide linkages are essentially all disulfide linkages. The product, a liquid oligomeric dimercaptan having a molecular weight of 1000-7000, may be cured with a metal oxide to form coatings and sealants. These conventional formal-based sealants suffer from relatively high moisture vapor transmission rates compared to butyl-based sealants and polyurethane sealants.

SUMMARY OF THE INVENTION

It is an object of this invention to provide liquid polysulfides from which sealants having much improved moisture vapor transmission rates, comparable to the polyurethane and butyl-based sealants, may be formulated. These have particular utility in insulated glass window units.

It is related object to provide such a liquid polysulfide which also has good curing characteristics.

These and other objects which will be apparent from the following description are achieved by a liquid polysulfide having the formula:
$HSCH_2CH_2OCH_2OCH_2C$-
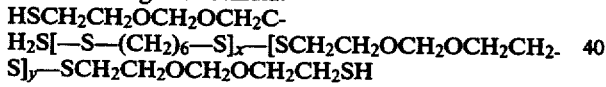
$S]_y$—$SCH_2CH_2OCH_2OCH_2CH_2SH$ wherein the molar ratio of x/y is from about 0.6:0.4 to about 0.7:0.3 or from about 1.5:1 to about 2.3:1.

DETAILED DESCRIPTION OF THE INVENTION

The hexylenedithio- moiety of the polysulfide has its origin in a dihalohexane wherein the halogens may be chlorine or bromine. The reaction of the dihalohexane and the bis-(2-chloroethyl formal) with the sodium polysulfide and the succeeding reduction are carried out in the conventional manner which is described in the Kirk & Othmer "Encyclopedia of Chemical Technology" Vol 18, pp 814–831, John Wiley & Sons (1982). The dihalohexane and the bis-(2-chloroethyl formal) are mixed in the mole ratio desired in the final product. In a preferred product, x is 0. 66 and y is 0.34. The reaction mixture suitably may contain from about 0.2 to about 2% by weight of a crosslinking agent such as trichloropropane, based on the total weight of the halogenated reactants.

The cured sealants of this invention have a permeability of less than 0.03 metric perms cm whereas the permeability attainable with conventional sealants is on the order of about 0.08 metric perms cm.

Curing agents for the liquid polysulfides may be selected from among the many conventional metal oxides and peroxides. The curable sealant compositions of this invention may contain the various types of inert materials commonly used in the sealant art in addition to the curing agents. Fillers, plasticizers, pigments, ultraviolet light stabilizers, cure accelerators, and the like. Sealant formulations employing the LP-2 and LP-32 polysulfides sold by Morton International, Inc. are well known and are taught in its product literature. These may be readily adapted to the new polysulfides of this invention.

The following examples illustrate preferred embodiments of the invention.

EXAMPLE 1

A mixture of 1010 mls. of an aqueous solution of 273.2 grams of sodium polysulfide (2.27 rank), 10 grams of Aerosol OS, 41.4 grams of magnesium chloride, and 5.9 grams of tricresyl phosphate was stirred and heated in a 3-liter flask fitted with a thermocouple, reflux condenser, and inlet tube to 80° C. A mixture of 117.7 grams (0.68 mole) of bis-2-chloroethyl formal and 204.8 grams (1.32 mole) of 1,6-dichlorohexane (Aldrich) was added in about 1 hour and the mixture was heated to the reflux temperature (106.5° C.) and held there for about 18 hours. The mixture was cooled and diluted with 2 liters of water before the resultant latex was allowed to settle. The supernatant liquid was removed and the latex was washed first with 1 liter and then seven times with 2 liters of water to yield 1604 grams of wet latex containing 297.7 grams of solids.

EXAMPLE 2

A latex made according to the general procedure of Example 1 weighing 1290.7 grams and having a 35.3% solids content was stirred and heated in a reaction vessel equipped with a thermocouple and reflux condenser to 85.3° C. before 253.5 parts of sodium sulfite and 29.5 parts of an aqueous solution of sodium hydrosulfide (containing 45.3% by weight of NaSH) were added in rapid succession. After one hour of stirring at 85° C. 40.9 parts of sodium bisulfite and the suspension was allowed to cool before washing 8 times with 2 liters of water. The supernatant was removed and then dried while being stirred for about 2 hours at a reduced pressure of about 2.5 mm Hg and a temperature of up to about 94° C. on a steam bath. A 90.9% yield of liquid polysulfide having an SH content of 2.14% was obtained.

EXAMPLE 3

One hundred parts of a liquid polysulfide made according to the general procedure of Example 2 are blended with 167 parts of a conventional sealant base formulation comprising 36 parts of a chlorinated paraffin (Unichlor 5722-Neville), 35 parts of coated, precipitated calcium carbonate having a particle size ranging from 0.02 to 0.1 microns, 82 parts of ground calcium carbonate having a particle size ranging from 2 to 8 microns, 2 parts of titanium dioxide, 1 part of silane adhesion promoter (Union Carbide A-187 and A-189), and 11 parts of toluene on a three-roll mill. The blend is cured with 23.6 parts of a curing paste containing 10 parts of active manganese dioxide ( Shepherds), 10.7 parts of Santicizer 278 plasticizer, 1.5 parts of platey talc, 0.3 part of carbon black, 1 part of lead oxide, and 0.1 part of diphenylguanidine at room temperature for 30 days and is pressed into 6"×6" sheets.

COMPARATIVE EXAMPLE 1

A liquid polysulfide made according to the general procedure of Example 2 except that 1,10-dibromodecane replaced the 1,6-dibromohexane and the mole ratio of the formal to the dihaloalkane was 0.50:0.50 is blended with the sealant base formulation of Example 3 and the sealant is cured and pressed in the same manner as in Example 3.

The permeability of the sealant of Example 3 is lower than that of the sealant of Comparative Example 1 according to ASTM Procedure F-1249-90.

By having thus described particular embodiments of the invention for illustrative purposes, it is not intended thereby to exclude other embodiments, whether specifically mentioned above or implied by the disclosure in general, from the scope of the following claims.

The subject matter claimed is:

1. A liquid polysulfide made by the reaction of sodium polysulfide with a mixture of a dihalohexane and bis-2-chloroethylformal in which the molar ratio of the dihalohexane and bis-2-chloroethylformal is from about 1.5:1 to about 2.3:1.

2. The polysulfide of claim 1 wherein the reaction mixture also contains from about 0.2 to about 2 % of a crosslinking agent, based on the total weight of the dihalohexane and bis-2-chloroethylformal.

* * * * *